June 12, 1973 W. H. JESSEL, JR., ET AL Plant Pat. 3,358
CHRYSANTHEMUM PLANT
Filed Aug. 25, 1971
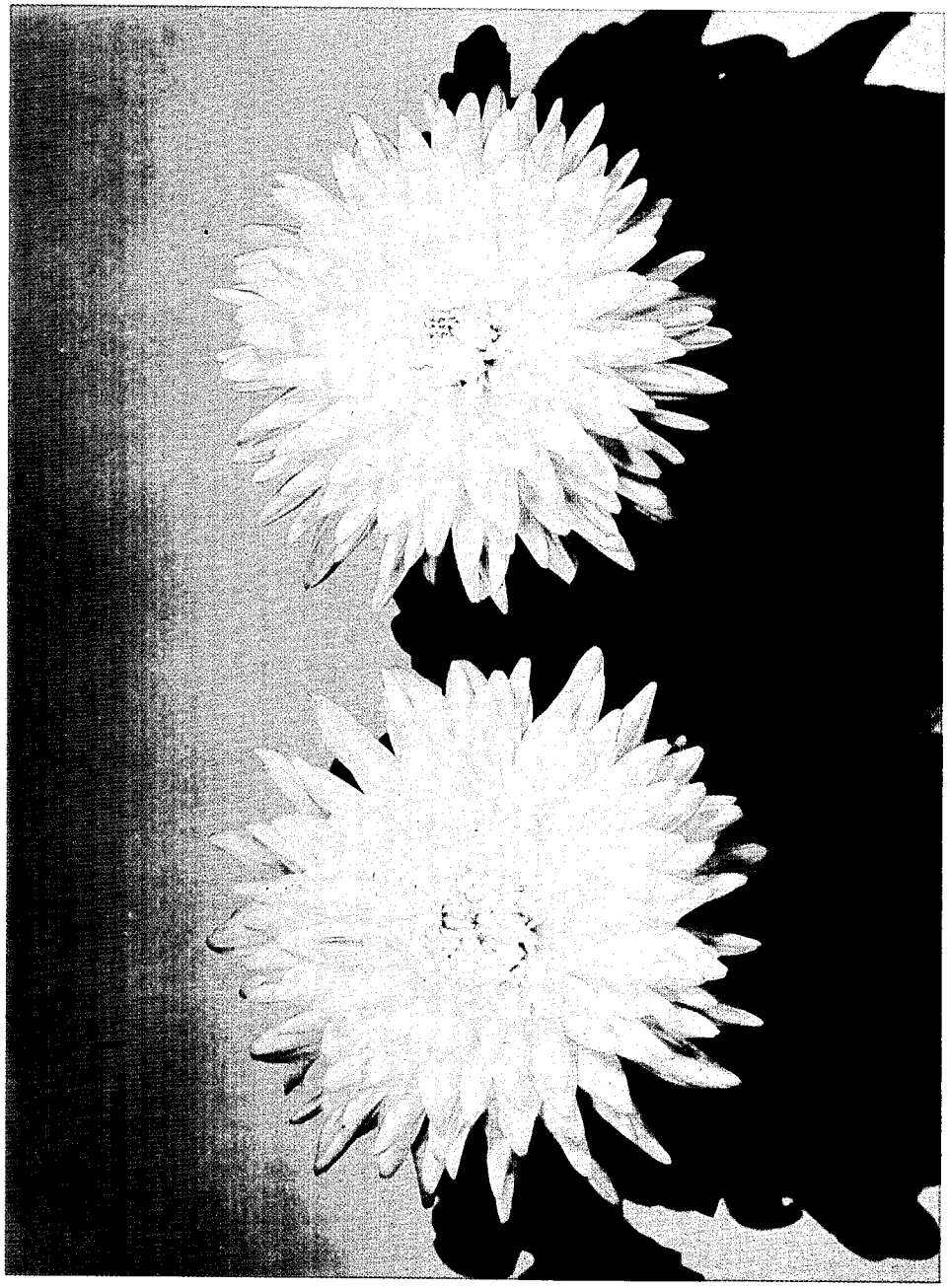

United States Patent Office

Plant Pat. 3,358

Patented June 12, 1973

3,358

CHRYSANTHEMUM PLANT

Walter H. Jessel, Jr., Doylestown, and William E. Duffett, Akron, Ohio, assignors to Yoder Brothers, Inc., Barberton Ohio

Filed Aug. 25, 1971, Ser. No. 175,011

Int. Cl. A01h *5/00*

U.S. Cl. Plt.—77 1 Claim

The present invention comprises a new and distinct cultivar of chrysanthemum plant which is a seedling of #60228–2×62966–1. Both parents are unpatented and are identified for breeding purposes by the above numbers to distinguish the same from other parents in the same program.

The new cultivar is similar in many respects to the unpatented but commercially well-known cultivar Neptune, having the same characteristics as Neptune of:

(1) A year-round recommended flowering period.
(2) Similar flower size.
(3) Decorative flower form and white flower color.
(4) Prominent stipules.

The new cultivar is distinguished from Neptune by the following characteristics, when grown under comparable conditions:

(1) Response is approximately 4–10 days earlier depending on the season of the year.
(2) A more vigorous variety which can be grown under medium rather than short treatment as Neptune normally is.
(3) Stronger, heavier stems.
(4) No pinking of the flowers with a cool finish of 60° or less.
(5) No longitudinal petal roll under low light and also high temperature finishes of 70°–75° or above, which conditions cause a reduction in flower size and contributes to an aged appearance on Neptune.
(6) No open center or significant petal reduction under low light or low temperature conditions.

(7) A wider, more spreading habit, when both varieties are grown and flowered with their recommended response and teratments.
(8) Averages one more break per plant.
(9) Foliage approximately one-quarter inch shorter in length.
(10) A lighter foliage color.
(11) Foliage less idented with less serration.

The new cultivar was selected from the progeny of the designated cross and when asexually reproduced by cuttings at Barberton, Ohio, has been found to retain its distinctive characteristics through successive propagations.

The new cultivar was selected from a flowering block of the parent cultivar at Barberton, Ohio; and when asexually reproduced by cuttings at Barberton, Ohio, has been found to retain its distinctive characteristics through successive propagations.

The new cultivar when grown in the vicinity of Barberton, Ohio, has a response period of approximately 8 weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern and western United States, and coastal California is from January through December; Florida, November through May.

The accompanying drawing illustrates the new cultivar, with the color being as nearly true as possible with color photographs of this type.

In the description which follows, color references are to the Munsell Color Book, 1963 edition, and comparisons are made with the cultivar Neptune. Where only a single value or description appears from the new cultivar, the same value or description applies also for the comparison cultivar Neptune.

Botanical classification: *Chrysanthemum morifolium*

| | Windsong | Neptune |
|---|---|---|
| Bloom: | | |
| Size | Approximately 4″ | |
| Fully expanded | Approximately 5″ | |
| Borne | Terminal on disbudded plants | |
| Stems | Very strong | Strong. |
| Form | Decorative | |
| Permanence | 10–14 days | |
| Color: | | |
| Center of flower | White, 10Y9/1 | Streaked pink on white 2.5RP5/12 with a cool finish or 60° or less to white, 7.5Y9/2 at finishing temperatures above this level. |
| Base of petals | White, N9.5/ | |
| Inside of petals | do | |
| Reverse of petals | do | |
| Tonality from a distance | White | |
| Discoloration | do | White streaked pink, 2.5RP5/12 on N9.5/ with a cool finish of 60° or less to white, 7.5Y9/2 at finishing temperature above this level. |
| Petals: | | |
| Texture | Smooth | |
| Appearance and form | Open at base, broad shallow keel, slightly recurving near apex, tapering to a blunt point. | Slightly open at base keeled at mid point, several ridges on bottom, 5/16″ wide. |
| Arrangement | Composite, whorled on a single receptacle | |
| Persistence | Resist shatter | |
| Fragrance | Typical chrysanthemum | |
| Reproductive organs: | | |
| Stamen, anthers | None | None to 25–30. |
| Pollen | do | None to scant. |
| Arrangement | Clustered in center of flower, if present | |
| Styles | Present ray florets | Present both ray and disc florets. |
| Length | Short | |
| Ovaries | At the base of petal attached to receptacle | |
| Plant: | | |
| Form | Herbaceous | |
| Growth | Spreading | Upright. |
| Height | Approximately 11″ when grown with 8 week medium treatment as defined in the Yoder timetables. | Approximately 12″ when grown with 9 week short treatment as defined in the Yoder timetables. |
| Spread | do | Approximately 5½″ when grown with 9 week short treatment as defined in the Yoder timetables. |

| | Windsong | Neptune |
|---|---|---|
| Foliage: | | |
| Top side | Dark green, 7.5GY3/4. | Very dark green, 5GY2/4. |
| Size | 3¾″ long, 2¼″ wide | 4″ long, 2½″ wide. |
| Quantity | Numerous | |
| Shape | Spatulate lobed | |
| Texture | Smooth | |
| Ribs and veins | Prominent | |
| Edge | Moderately indented | Indented. |
| Serration | Slight | Moderate. |
| Under side | Light green, 5GY5/4 | Light green, 10GY5/4. |
| Stipules | Prominent | |

We claim:

1. A new and distinct cultivar of chrysanthemum characterized particularly as to uniqueness when compared to the cultivar Neptune by its response which is approximately 4–10 days earlier depending on the season of the year, a more vigorous variety which can be grown under medium rather than short treatment, stronger, heavier stems, no pinking of the flowers with a cool finish of 60° or less, no longitudinal petal roll under low light and also high temperature finishes of 70°–75° or above, no open center or significant petal reduction under low light or low temperature conditions, a wider, more spreading habit when both varieties are grown and flowered with their recommended response and treatments, average of one more break per plant, foliage approximately one-quarter inch shorter in length, a lighter foliage color, with the foliage being less indented with less serration.

No references cited.

ROBERT E. BAGWILL, Primary Examiner

UNITED STATES PATENT OFFICE

CERTIFICATE OF CORRECTION

Patent No. PP-3,358 Dated June 12, 1973

Inventor(s) WALTER H. JESSEL, JR. and WILLIAM E. DUFFETT

It is certified that error appears in the above-identified patent and that said Letters Patent are hereby corrected as shown below:

In column 2, line 3, "teratments" should be --treatments--; line 8, "idented" should be --indented--; line 36, "from" should be --for--.

In the tabulation, opposite "Color: , Center of flower", under "Neptune", "finish or 60° or less" should read --finish of 60° or less--.

Signed and sealed this 1st day of October 1974.

(SEAL)
Attest:

McCOY M. GIBSON JR.
Attesting Officer

C. MARSHALL DANN
Commissioner of Patents